(12) United States Patent
Weismann et al.

(10) Patent No.: US 7,798,145 B2
(45) Date of Patent: Sep. 21, 2010

(54) DEVICE AND PROCESS FOR BREATH-SUPPORTING RESPIRATION

(75) Inventors: Dieter Weismann, Gross Grönau (DE); Hermann Hopermann, Badendorf (DE)

(73) Assignee: Dräger Medical AG & Co. KG, Lübeck (DE)

( * ) Notice: Subject to any disclaimer, the term of this patent is extended or adjusted under 35 U.S.C. 154(b) by 1063 days.

(21) Appl. No.: 11/461,092

(22) Filed: Jul. 31, 2006

(65) Prior Publication Data

US 2007/0062530 A1  Mar. 22, 2007

(30) Foreign Application Priority Data

Sep. 22, 2005  (DE) ............... 10 2005 045 127

(51) Int. Cl.
*A62B 7/00* (2006.01)
*F16K 31/02* (2006.01)

(52) U.S. Cl. .................... 128/204.23; 128/204.18; 128/204.21

(58) Field of Classification Search ........................... 128/204.23–207.29, 200.24, 203.12–203.14, 128/203.29, 204.18–204.21
See application file for complete search history.

(56) References Cited

U.S. PATENT DOCUMENTS

| 5,582,163 | A * | 12/1996 | Bonassa ............... | 128/204.26 |
| 5,660,171 | A * | 8/1997 | Kimm et al. ........... | 128/204.23 |
| 6,192,885 | B1 * | 2/2001 | Jalde .................... | 128/205.24 |
| 6,412,483 | B1 * | 7/2002 | Jones et al. ............ | 128/205.11 |
| 7,562,657 | B2 * | 7/2009 | Blanch et al. .......... | 128/204.23 |
| 2003/0230307 | A1 * | 12/2003 | DeVries et al. ........ | 128/204.18 |
| 2005/0087190 | A1 * | 4/2005 | Jafari et al. ............ | 128/204.21 |

FOREIGN PATENT DOCUMENTS

EP  0459647 B1  12/1991

\* cited by examiner

*Primary Examiner*—Steven O Douglas
*Assistant Examiner*—Rachel T Young
(74) *Attorney, Agent, or Firm*—McGlew and Tuttle, P.C.

(57) ABSTRACT

A respirator for breath-supporting respiration has improved sensitivity of triggering breathing support. A pre-inspiratory inspiratory gas flow is set, which flows off via the expiration valve (9). The closing pressure $p_v$ of the expiration valve is measured with a pressure sensor (11) in the process. The gas flow is increased in case of an inspiratory effort of the patient to the extent that the closing pressure $p_v$ of the expiration valve (9) is restored. Breath support is generated when the difference between the preset gas flow and the gas flow that is needed to maintain the closing pressure $p_v$ at a constant level exceeds a predetermined threshold value.

9 Claims, 2 Drawing Sheets

DEVICE AND PROCESS FOR BREATH-SUPPORTING RESPIRATION

CROSS REFERENCE TO RELATED APPLICATIONS

This application claims the benefit of priority under 35 U.S.C. §119 of German Patent Application DE 10 2005 045 127.6 filed Sep. 22, 2005, the entire contents of which are incorporated herein by reference.

FIELD OF THE INVENTION

The present invention pertains to a device for breath-supporting respiration and to a process for controlling a respirator (also known as a ventilator).

BACKGROUND OF THE INVENTION

To apply breath-supporting respiration, pressure- or volume-controlled respirators are known, which make possible a plurality of respiration functions during the inspiration phases and expiration phases.

In prior-art respirators, the inspiration valve is closed and the expiration valve is opened at the beginning of expiration. The expiration valve is then actuated such that a predetermined end-expiratory pressure becomes established in the expiration line. This pressure is usually measured near the end of the expiration phase, when the expiration gas flow has reached a low value. Based on inevitable tolerances, the pressure actually measured always deviates from the preset value, and one seeks to actuate the expiration valve such that the deviation between the measured and preset pressures will be as little as possible. This pressure, hereinafter called the closing pressure of the expiration valve, can only be measured accurately as long as a small gas flow is flowing over the expiration valve.

Respirators also have mechanisms, hereinafter called "triggers," for recognizing the patient's inspiratory efforts in order to trigger mechanical breathing support. The trigger is an important circuit element of a respirator and is a prerequisite for the patient to be able to communicate the initial pulse for the mechanical respiration stroke to the respirator. The trigger can be triggered by a pressure drop in the expiration line, which is generated by the patient's inspiration effort. The trigger threshold must be set such that it is below the end-expiratory pressure level. However, on the other hand, it also must not be so low that the patient would have to exert an excessively great inspiratory effort.

A continuous flow rate from the expiration valve is set in a respirator known from EP 459 647 B1. The gas flow is measured in the inspiration line and in the expiration line by means of two gas flow sensors, and the difference is determined. When the patient begins to breathe, part of the gas flow enters the patient's lungs and the gas flow in the expiration line is correspondingly reduced. If the difference of the gas flow exceeds a certain threshold value, the expiration valve is closed by a control unit of the respirator and an inspiration stroke is triggered. The pre-inspiratory continuous flow rate is restored at the end of the expiration.

To prevent the pressure from dropping during the patient's inspiratory effort in the prior-art respirator, the continuous gas flow must be distinctly higher than the patient's inspiratory gas flow to be recognized. Since the gas flows are measured with two different sensors, the measuring uncertainties of the sensors limit the sensitivity to recognize an inspiratory effort. High continuous gas flow rate also impairs the determination of the patient's respiratory minute volume, because the inspiration stroke applied must be determined from the difference of the gas flow in the inspiration line and that in the expiration line. The sensitivity of triggering is therefore not so high as it would be necessary for breathing support for critically ill patients.

SUMMARY OF THE INVENTION

The basic object of the present invention is to improve a respirator in terms of the sensitivity of triggering and to provide a process for controlling a respirator.

According to the invention, a device is provided for breath-supporting respiration. The device includes a breathing gas source, an expiration valve, an inspiration line from the breathing gas source to a patient, an expiration line from the patient to the expiration valve and a feed means for feeding breathing gas, which is arranged downstream of the breathing gas source and can be actuated. A flow sensor is provided in the expiration line. The flow sensor supplies a measured breathing gas flow value $dV_{em}/dt$. A pressure sensor is provided on the incoming flow side of the expiration valve for determining a breathing gas pressure measured value $p_{vm}$. A first control unit sets an expiration valve closing pressure $p_v$ from the measured flow value $dV_{em}/dt$ and the breathing gas measured value $p_{vm}$ according to the presetting of a pressure set point. A second control loop with the feed means as the final control element sets a gas flow for determining the expiration valve closing pressure $p_v$ according to the presetting of a set point for a pre-inspiratory inspiratory gas flow $dV_{emin}/dt$ with the breathing gas measured flow value $dV_{em}/dt$ as the actual value. A control means is provided designed to generate breathing support when the pre-inspiratory gas flow $dV_{isoll}/dt$ necessary for maintaining the closing pressure $p_v$ exceeds a preset threshold value.

The first control unit may advantageously be designed to integrate the internal resistance of the expiration valve in the setting of the closing pressure $p_v$. The control means may be designed to generate breathing support when the difference between the preset set point for the pre-inspiratory inspiratory gas flow $dV_{emin}/dt$ and the gas flow $dV_{isoll}/dt$ necessary for maintaining the closing pressure $p_v$ exceeds a present threshold value.

The advantage of the present invention is essentially that the closing pressure $p_v$ is measured not only at the end of expiration, but, by means of a small continuous gas flow, also before an expected inspiration, and a control loop for setting a set point for the closing pressure is coupled with the feed means arranged upstream of the inspiration line such that when the closing pressure $p_v$ drops, because of the patient's inspiration effort, more breathing gas is supplied and the closing pressure is restored. If the difference between the preset pre-inspiratory gas flow and the breathing gas flow supplied exceeds a predetermined threshold value, an inspiration stroke is triggered. Only a small gas flow, which must be somewhat higher than the lower measuring limit of the flow sensor, is necessary for setting the closing pressure $p_v$. Therefore, the continuous gas flow also compromises the measurement of the respiration stroke volume applied only slightly. If the continuous gas flow drops below the measuring threshold, for example, because of an inspiratory effort on the part of the patient, only so much breathing gas is supplied from the feed means that the preset closing pressure $p_v$ will again be reached. Artifacts, which briefly cause a pressure drop, do not compromise triggering, because only as much breathing gas is supplied as is necessary to exceed the lower measuring threshold of the flow sensor. The inspiration stroke is triggered only when the difference between the preset pre-inspiratory gas flow rate and the breathing gas flow supplies exceeds a predetermined threshold value. As an alternative, it is also possible to compare only the breathing gas flow supplied with a threshold value.

The process according to the present invention is characterized by the following steps:

A pre-inspiratory gas flow corresponding to the presetting of a set point is set with a feed means for breathing gas and is allowed to flow off via the expiration valve at a preset closing pressure.

The closing pressure is measured as a measured pressure value with a pressure sensor.

The gas flow is increased with the feed means when the measured pressure value drops because of an inspiratory effort on the part of the patient until the preset closing pressure is again reached.

Breathing support is generated with a control means when the pre-inspiratory gas flow $dV_{isoll}/dt$ necessary to maintain the closing pressure $p_v$ exceeds a predetermined threshold value.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
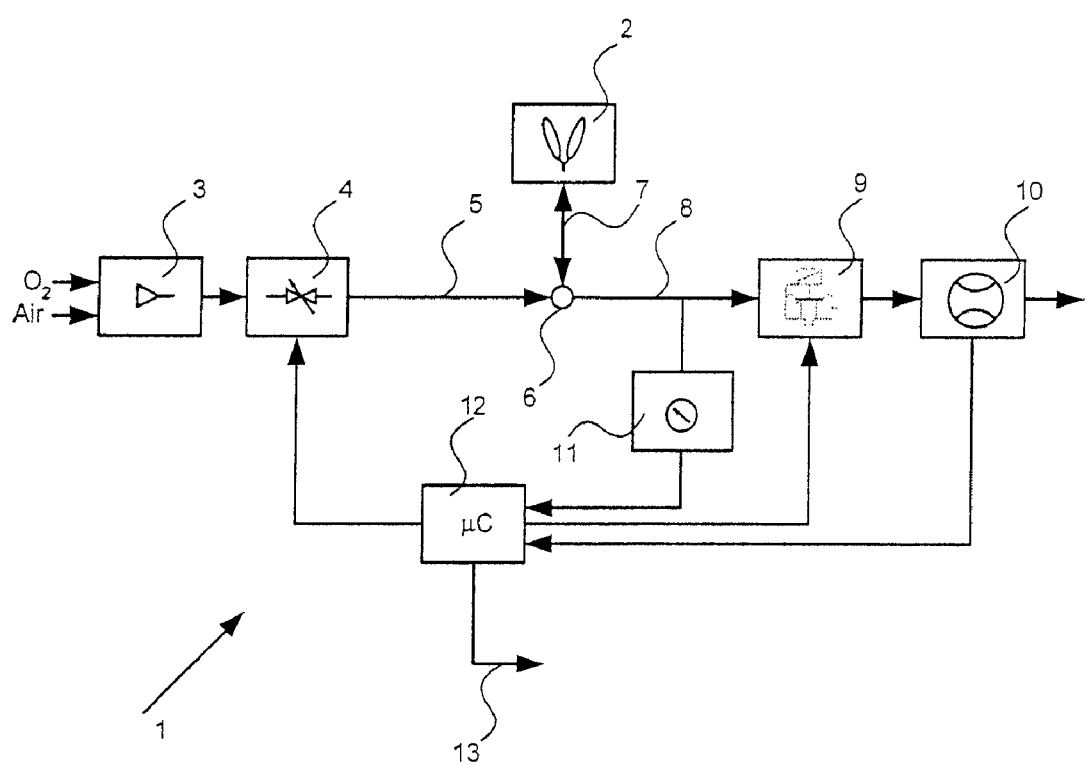
FIG. 1 is a schematic view showing a respirator design according to the invention.

Referring to the drawings in particular, FIG. 1 illustrates a respirator 1 for supplying a patient 2 with breathing gas. A gas mixer 3, acting as a breathing gas source, generates a breathing gas mixture from oxygen (an oxygen source) and air. The breathing gas mixture enters an inspiration line 5 via a dispensing valve 4, which can be actuated and acts as a feed means. The inspiration line 5 is connected at a branching point 6 to a breathing gas line 7 leading to the patient (patient connection) 2 and to an expiration line 8. The expiration line 8 ends at an expiration valve 9. The gas flow of the expired gas is measured on the discharge side of the expiration valve 9 with a flow sensor 10. A pressure sensor 11 arranged on the incoming flow side of the expiration valve 9 detects the pressure $p_v$ in the expiration line 8. The dispensing valve 4, the expiration valve 9, the flow sensor 10 and the pressure sensor 11 are connected to a central control and calculating unit 12, with which a triggering signal is triggered via a line 13 for initiating an inspiration stroke.

Figure 2:
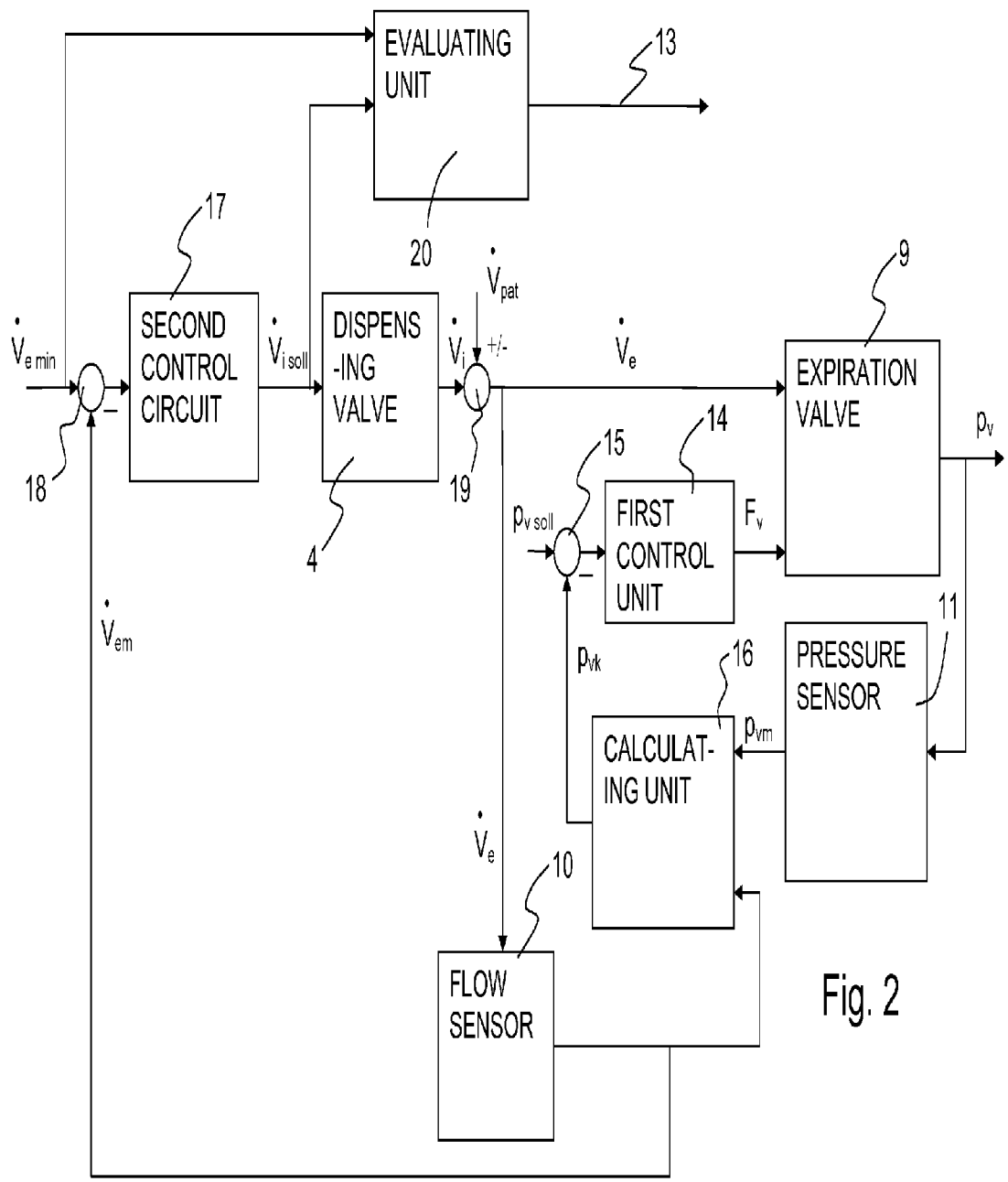
FIG. 2 is a schematic view showing the control structure of the respirator according to FIG. 1.

FIG. 2 illustrates the control structure of the respirator 1 according to FIG. 1. Identical components are designated by the same reference numbers as in FIG. 1.

Via a first comparison point 15, a first control unit 14 receives the difference between a preset set point for the expiration valve closing pressure $p_{vsoll}$ and a closing pressure $p_{vk}$, which is corrected by means of the known internal resistance of the expiration valve 9. The calculating unit 16 receives as input variables the measured expiratory pressure value $p_{vm}$ measured with the pressure sensor 11 and the measured flow value $dV_{em}/dt$ determined with the flow sensor 10.

A second control unit 17 supplies the actuating signal $dV_{isoll}/dt$ for the dispensing valve 4. The second control circuit 17 receives for this, via a second comparison point 18, the difference between the preset set point for a minimum expiratory flow $dV_{emin}/dt$ and the measured flow value $dV_{em}/dt$ measured with the flow sensor 10 as an input variable. Depending on the direction of the breathing flow, the sum or the difference of the gas flow $dV/dt$ supplied by the dispensing valve 4 and the patient gas flow $dV_{pat}/dt$, which sum or difference enters the expiration line 8 as an expiratory gas flow $dV_e/dt$, is formed in the breathing gas line 7 at the branching point 6. This difference is formed in the control structure at the third comparison point 19.

At the beginning of an expected inspiration by the patient, the preset set point $dV_{emin}/dt$ is compared with the actuating signal $dV_{isoll}/dt$ of the dispensing valve 4 in an evaluating unit 20. When the difference of the two variables exceeds a preset threshold value, a trigger signal is generated via the line 13 for initiating an inspiration stroke.

The respirator according to the present invention operates as follows:

At the beginning of an inspiration stroke, the breathing gas is fed via the dispensing valve 4 to the patient 2 until the preset breathing stroke volume is reached. The expiration valve 9 is closed during the inspiration. During expiration, the expiration valve 9 receives a preset set point for the end-expiratory closing pressure $p_{vsoll}$ to be set via the first comparison point 15.

Via the second comparison point 18, a preset set point for a minimum expiratory flow $dV_{emin}/dt$ is sent to the second control unit 17, so that a low gas flow is dispensed with the dispensing valve 4 as soon as the expiratory gas flow drops below the lower measuring limit of the flow sensor 10. The gas flow makes it possible to set the closing pressure $p_v$ of the expiration valve 9 to the preset set point $p_{vsoll}$. The first control unit 14 supplies for this a manipulated variable $F_v$ for the closing pressure to the expiration valve 9. The gas flow $dV_e/dt$ in the expiration line 8 drops during an inspiration effort on the part of the patient and the preset set point $dV_{isoll}/dt$ for the dispensing valve 4 is increased by the second control unit 17 to maintain the closing pressure $p_v$ until the closing pressure $p_e$ is again restored. The difference between $dV_{emin}/dt$ and $dV_{isoll}/dt$ is evaluated in the evaluating unit 20 to determine whether a threshold value is exceeded. When the threshold value is exceeded, a trigger signal is sent via the line 13 to initiate an inspiration stroke.

While specific embodiments of the invention have been shown and described in detail to illustrate the application of the principles of the invention, it will be understood that the invention may be embodied otherwise without departing from such principles.

What is claimed is:

1. A device for breath-supporting respiration, the device comprising:

a breathing gas source;

an expiration valve;

an inspiration line from said breathing gas source to a patient;

an expiration line from the patient to said expiration valve;

a feed means for feeding breathing gas, which is arranged downstream of said breathing gas source and can be actuated;

a flow sensor for sensing flow in said expiration line, and for supplying a measured breathing gas flow value $dV_{em}/dt$;

a pressure sensor for determining a breathing gas pressure measured value $p_{vm}$ on the incoming flow side of said expiration valve;

a first control for acting on said expiration valve for setting an expiration valve closing pressure $p_v$ based on said measured breathing gas flow value $dV_{em}/dt$ and said breathing gas pressure measured value $p_{vm}$ and according to a presetting of a pressure set point;

a second control forming a control loop and acting on said feed means as a final control element, said second control setting a gas flow, not equal to zero, with said feed means for determining the expiration valve closing pressure $p_v$, said setting of the gas flow being based on a presetting of a set point for a pre-inspiratory inspiratory gas flow $dV_{emin}/dt$, not equal to zero, and said breathing gas measured flow value $dV_{em}/dt$ as the actual value; and a control means for generating breathing support by acting on said feed means to provide a breathing support inspiration flow higher than said setting of the gas flow when the pre-inspiratory gas flow $dV_{isoll}/dt$ necessary for maintaining the closing pressure $p_v$ exceeds a preset threshold value.

2. A device in accordance with claim 1, wherein said first control includes a correction based on an internal resistance of said expiration valve for acting on said expiration valve in the setting of said closing pressure $p_v$.

3. A device in accordance with claim 1, wherein said control means generates breathing support when a difference between the preset set point for said pre-inspiratory inspiratory gas flow $dV_{emin}/dt$ and said gas flow $dV_{isoll}/dt$ necessary for maintaining said closing pressure $p_v$ exceeds a present threshold value.

4. A process for controlling a respirator, the process comprising:
   providing a breathing gas source;
   providing an expiration valve;
   providing an inspiration line from the breathing gas source to a patient;
   providing an expiration line from the patient to the expiration valve;
   providing a feed means arranged downstream of the breathing gas source with the feed means being actuatable;
   providing a flow sensor sensing flow in the expiration line and for supplying a measured breathing gas flow value $dV_{em}/dt$;
   providing a pressure sensor sensing pressure on the incoming flow side of the expiration valve;
   setting of a pre-inspiratory gas flow, not equal to zero and corresponding to a presetting of a set point, $dV_{emin}/dt$;
   allowing the flow to flow off via the expiration valve at a preset closing pressure $p_v$;
   measuring the closing pressure $p_v$ as a measured pressure valve $p_{vm}$ with the pressure sensor;
   increasing the pre-inspiratory gas flow with the feed means when the measured pressure value $p_{vm}$ drops because of an inspiration effort on the part of the patient until the preset closing pressure $p_v$ is restored; and
   generating breath support with a control means acting on said feed means to provide a breathing support inspiration flow higher than said setting of the gas flow and said pre-inspiratory gas flow when the pre-inspiratory gas flow $dV_{isoll}/dt$ necessary to maintain the closing pressure $p_v$ exceeds a preset threshold value.

5. A process in accordance with claim 4, wherein breath support is generated when the difference between the preset set point for the pre-inspiratory inspiratory gas flow $dV_{emin}/dt$ and the gas flow $dV_{isoll}/dt$ necessary to maintain the closing pressure $p_v$ exceeds a preset threshold value.

6. A process in accordance with claim 5, wherein:
   said step of allowing the flow to flow off via the expiration valve at a preset closing pressure $p_v$ includes using a first control for acting on said expiration valve for setting the expiration valve closing pressure $p_v$ based on said measured breathing gas flow value $dV_{em}/dt$ and said breathing gas pressure measured value $p_{vm}$ and according to a presetting of a pressure set point; and
   said step of increasing the gas flow with the feed means when the measured pressure value $p_v$ drops because of an inspiration effort on the part of the patient includes using a second control forming a control loop and acting on said feed means as a final control element, said second control setting a gas flow with said feed means for determining the expiration valve closing pressure $p_v$, said setting of the gas flow being based on a difference between a presetting of a set point for a pre-inspiratory inspiratory gas flow $dV_{emin}/dt$ and said breathing gas measured flow value $dV_{em}/dt$ as the actual value.

7. A device for breath-supporting respiration, the device comprising:
   a breathing gas source;
   an expiration valve;
   an inspiration line from said breathing gas source to a patient;
   an expiration line from the patient to said expiration valve;
   a feed means for feeding breathing gas, which is arranged downstream of said breathing gas source and can be actuated;
   a flow sensor for sensing flow in said expiration line, and for supplying a measured breathing gas flow value $dV_{em}/dt$;
   a pressure sensor for determining a breathing gas pressure measured value $p_{vm}$ on the incoming flow side of said expiration valve;
   a first control forming a first control signal for acting on said expiration valve for setting an expiration valve closing pressure $p_v$ based on a difference between a presetting of a pressure set point $p_{v\,soll}$ and a closing pressure based on said measured breathing gas flow value $dV_{em}/dt$ and said breathing gas pressure measured value $p_{vm}$;
   a second control forming a second control signal $dV_{isoll}/dt$ for a minimum expiratory flow based on a difference between a set point for a pre-inspiratory gas flow $dV_{emin}/dt$, not equal to zero, and said measured actual breathing gas flow value $dV_{em}/dt$, said second control signal $dV_{isoll}/dt$ acting on said feed means for setting a gas flow for determining the expiration valve closing pressure $p_v$; and
   means for generating a trigger signal for acting on said feed means to provide a breathing support inspiration flow when said second control signal $dV_{isoll}/dt$ for maintaining the closing pressure $p_v$ exceeds a preset threshold value.

8. A device in accordance with claim 7, wherein said means for generating a trigger signal comprises an evaluating unit evaluating a difference between $dV_{emin}/dt$ and $dV_{isoll}/dt$ to determine whether a threshold value is exceeded wherein when the threshold value is exceeded, the trigger signal is sent via a line to initiate an inspiration stroke providing the breathing support inspiration flow higher than said setting of the gas flow and for closing said expiration valve during inspiration.

9. A device in accordance with claim 8, wherein said first control also includes a correction based on an internal resistance of said expiration valve for forming said first control signal, based on the difference between the presetting of the pressure set point $p_{v\,soll}$ and a closing pressure $p_{vk}$ which is correlated by means of the known internal resistance of the expiration valve.

* * * * *